United States Patent
Rinderknecht et al.

(10) Patent No.: US 8,092,365 B2
(45) Date of Patent: Jan. 10, 2012

(54) RESONANT MULTILAYERED IMPEDANCE PUMP

(75) Inventors: Derek Rinderknecht, Arcadia, CA (US); Morteza Gharib, San Marino, CA (US); Laurence Loumes, Marscille (FR); Arian Soroush Forouhar, Pasadena, CA (US); Anna Hickerson, Altadena, CA (US)

(73) Assignee: California Institute of Technology, Pasadena, CA (US)

( * ) Notice: Subject to any disclaimer, the term of this patent is extended or adjusted under 35 U.S.C. 154(b) by 706 days.

(21) Appl. No.: 11/621,065

(22) Filed: Jan. 8, 2007

(65) Prior Publication Data

US 2007/0177997 A1  Aug. 2, 2007

Related U.S. Application Data

(60) Provisional application No. 60/756,704, filed on Jan. 6, 2006.

(51) Int. Cl.
*A61M 1/12* (2006.01)

(52) U.S. Cl. ............ 600/18; 417/394; 417/412; 600/16; 623/3.1; 623/3.11; 623/3.16; 623/3.21

(58) Field of Classification Search ............... 417/394, 417/412; 623/3.1, 3.11, 3.16, 3.17, 3.21; 600/16, 18
See application file for complete search history.

(56) References Cited

U.S. PATENT DOCUMENTS

| | | | |
|---|---|---|---|
| 3,677,667 A * | 7/1972 | Morrison | ............... 417/474 |
| 6,254,355 B1 | 7/2001 | Gharib | |
| 6,278,847 B1 | 8/2001 | Gharib et al. | |
| 6,506,025 B1 * | 1/2003 | Gharib | |
| 6,580,503 B2 | 6/2003 | Gharib et al. | |
| 6,582,208 B2 | 6/2003 | Gharib | |
| 6,608,668 B2 | 8/2003 | Gharib et al. | |
| 6,672,847 B2 * | 1/2004 | Dooley | ................ 417/412 |
| 6,679,687 B2 | 1/2004 | Gharib | |
| 6,717,172 B2 | 4/2004 | Gharib et al. | |
| 6,956,230 B1 | 10/2005 | Gharib et al. | |
| 7,006,132 B2 | 2/2006 | Pereira et al. | |
| 7,033,132 B2 | 4/2006 | Gharib | |
| 7,163,385 B2 | 1/2007 | Gharib et al. | |
| 2003/0233143 A1 | 12/2003 | Gharib et al. | |
| 2004/0008853 A1 * | 1/2004 | Pelrine et al. | ................ 381/191 |
| 2004/0101414 A1 * | 5/2004 | Gharib et al. | ................ 417/53 |
| 2004/0151607 A1 | 8/2004 | Gharib | |
| 2004/0193035 A1 | 9/2004 | Gharib | |
| 2005/0275494 A1 | 12/2005 | Gharib et al. | |
| 2005/0277865 A1 | 12/2005 | Gharib et al. | |
| 2006/0084835 A1 * | 4/2006 | Laufer | ........................ 600/16 |
| 2006/0195180 A1 | 8/2006 | Kheradvar et al. | |
| 2006/0196642 A1 | 9/2006 | Gharib et al. | |
| 2006/0209193 A1 | 9/2006 | Pereira et al. | |
| 2006/0216173 A1 | 9/2006 | Kheradvar et al. | |
| 2007/0038016 A1 | 2/2007 | Gharib et al. | |

* cited by examiner

OTHER PUBLICATIONS

"Electrically Stimulated Bilayer Hydrogels as Muscles" by Paul Calvert et al. from SPIE Conference on Electroactive Polymer Actuators and Devices, SPIE vol. 3669, pp. 236-241, Mar. 1999.*

*Primary Examiner* — Scott Getzow
*Assistant Examiner* — Joseph Dietrich
(74) *Attorney, Agent, or Firm* — Law Office of Scott C. Harris, Inc.

(57) ABSTRACT

A multilayered impedance pump is formed by an inner tube and an outer tube which have different mechanical characteristics. The outer tube is relatively stiff, and can be used for a structural material. The inner tube is excitable, and a gel is placed between the inner and outer tube. The actuator actuates the gel to cause pressure waves along the inner tube.

13 Claims, 2 Drawing Sheets

BLOOD FLOW

BLOOD FLOW

BLOOD FLOW

RESONANT MULTILAYERED IMPEDANCE PUMP

CROSS-REFERENCE TO RELATED APPLICATIONS

This application claims priority to U.S. Provisional Application 60/756,704, filed Jan. 6, 2006. The disclosure of the prior application is considered part of (and is incorporated by reference in) the disclosure of this application.

BACKGROUND

The general structure and techniques, and more specific embodiments which can be used to effect different ways of carrying out the more general goals, are described herein.

U.S. Pat. No. 6,254,355 discloses a pump that pumps fluid based on differences in fluidic characteristics, e.g., fluidic impedance, between various parts.

Different applications for this impedance pump have been disclosed. The pump can be used to pump fluids within the body cavity. This pump may be very useful in biomedical applications since it can be a very energy efficient device, and can operate without any valve or impeller, or any structure on the inside of the tube or lumen.

SUMMARY

The present application describes a new impedance pump with multiple walls.

In an embodiment, this impedance pump is formed of an inner lumen and an outer lumen with a material between the inner and outer lumens that can transmit forces.

In another embodiment, waves are used that can constructively interfere, to allow a relatively small actuation wave to add and become a larger amplitude wave that is induced on the inner lumen.

DETAILED DESCRIPTION

Figure 1:
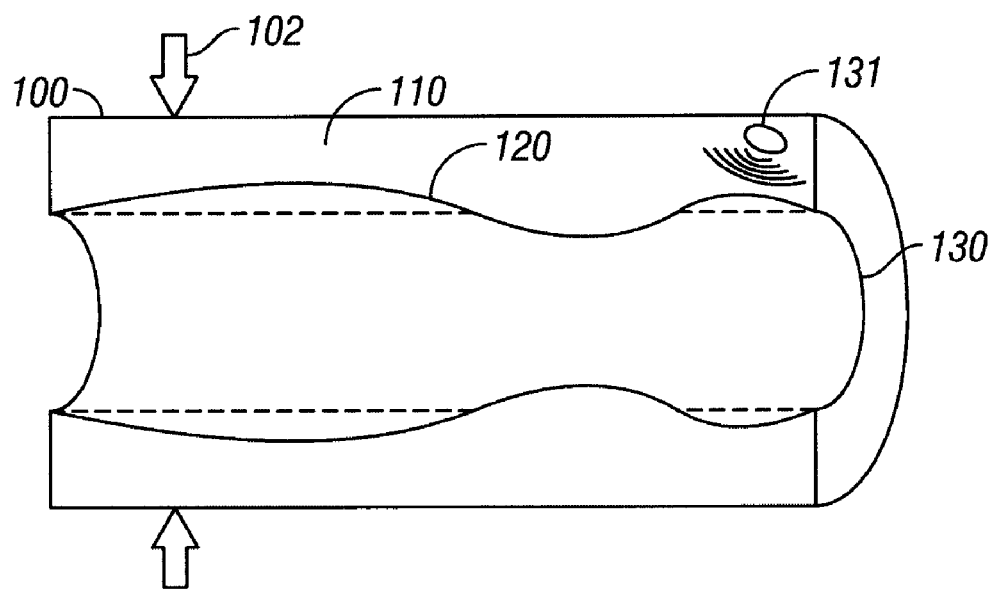
FIG. 1 shows a side view of a multilayered pump.
Figure 2:
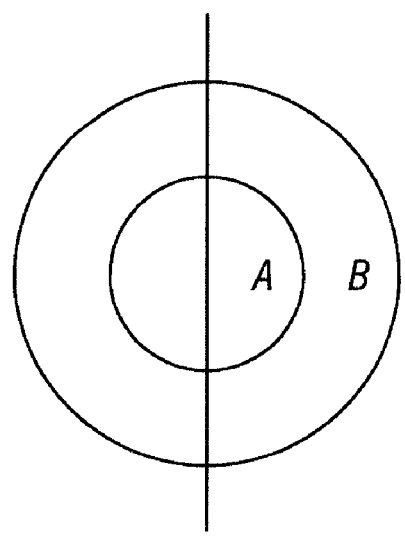
FIG. 2 shows a cross-sectional view of the pump along the line 2-2 in FIG. 1.

FIGS. 1-2 illustrate an embodiment of a double-walled impedance pump. In the embodiment, a first, inner lumen 120 is formed of a material that is elastically deformable. The inner lumen holds the fluid that is desired to be pumped. The first lumen 120 is surrounded by a second substantially unbending, e.g., rigid walled lumen 100.

The space between the inner lumen 120 and outer lumen 100 is filled with a fluid material 110. For example, the fluid material 110 may be a gel that has mechanical properties allowing it to transmit periodically applied forces. The fluid 110 may resonate at a resonant frequency (or frequencies) of the system. The fluid 110 preferably has a viscosity higher than 1.5 centi-Poise (cP). The gel can be any material than can transmit the force from an actuator to the flexible walled tube 120, however. Therefore, this application contemplates using fluids with gel-like consistencies, but also fluids with water-like consistencies, e.g., a viscosity of around 1 cP. Any fluid that can transmit applied force waves can be used.

The resonant motion of the gel material 110 causes little or no motion to the second surrounding lumen 100. Rather, a small amplitude excitation acting within the gel area between the lumens 100, 120 is, in effect, amplified by constructive interference caused by wave reflection at the boundary between the lumens. The amplitude amplification must be obtained by changing characteristics of the excitation, until the constructive interference is obtained. The system is also preferably operated at a resonant frequency. If so, this allows a small amplitude excitation within the area to be greatly amplified.

The embodiment shows two lumens interacting with each other in this way, but it should be understood that there can be 3, 4, 5, or any number of lumens which operate in an analogous way.

Any wave reflection boundary can be included as part of the system and can become part of the system and the resonant effect. Trial and error may be used to find optimum combinations.

The embodiment uses a flexible lumen 120 which receives an asymmetric excitation. Both ends of the lumens are fluidically coupled to sections of varying fluidic characteristics, e.g. fluidic compliance, geometry or any other physical property. In the embodiment of FIG. 2, one end of the lumens is closed.

The connection area between the lumens and the other materials creates a reflection site which causes fluidic wave reflection.

The excitation is carried out over a specific range of frequencies which can cause the potential for constructive wave interactions. When the proper interactions occur, a low amplitude excitation of the gel is effectively amplified into a larger amplitude surface wave that is formed on the inner surface of the inner lumen 120. This, in turn, creates a pressure gradient to drive fluid flow of fluid 110 within the inner lumen 120.

In addition, by selecting the excitation frequency to a frequency that causes resonant activity, the surface wave, and hence pumping may be greatly increased.

In operation, a low amplitude wave is created on or near the outer lumen 100, but preferably inside of the lumen 100. For example, a low amplitude wave may be created at the location 102, or at the location 131. The external layer 100 is a relatively stiff but compliant structure. Even though the structure is compliant, it is not dispensable, enabling it to be used within a body cavity. The material is referred to herein as being substantially unbending.

The low amplitude excitation avoids exciting the outer lumen, hence enabling its use in applications where high amplitude excitations could be harmful.

The low amplitude excitation at either of areas 102 or 131 may be caused by any of a number of different technologies including piezoelectric, electromagnetic, or electrostatic induction. Alternatively, the low amplitude wave may be created sonically or ultrasonically.

The low amplitude wave preferably is applied at a frequency that causes resonance within an internal gel layer 110 that is between the outer surface 100 and the inner surface 120. The resonant frequency may be found, for example, by trial and error.

Moreover, the gel allows the low amplitude excitation waves to be converted to large amplitude surface waves through the resonant reaction and through the wave reflection at an end surface 130. The small amplitude waves combine to large amplitude waves, which themselves propagate in a relatively soft gelatinous layer 120, and are effectively amplified by the constructive interference.

This pump may be used as an auxiliary heart pump, or as an aortic pump to serve as a replacement for current balloon pump designs. An advantage of this pump is that the outer surface 100 is relatively stiff, and therefore it can be used where structurally needed. A robust assistance device may be used to augment the impaired cardiac pumping capability to replace current long-term pumps that added complication in both use and implementation.

Figure 3:
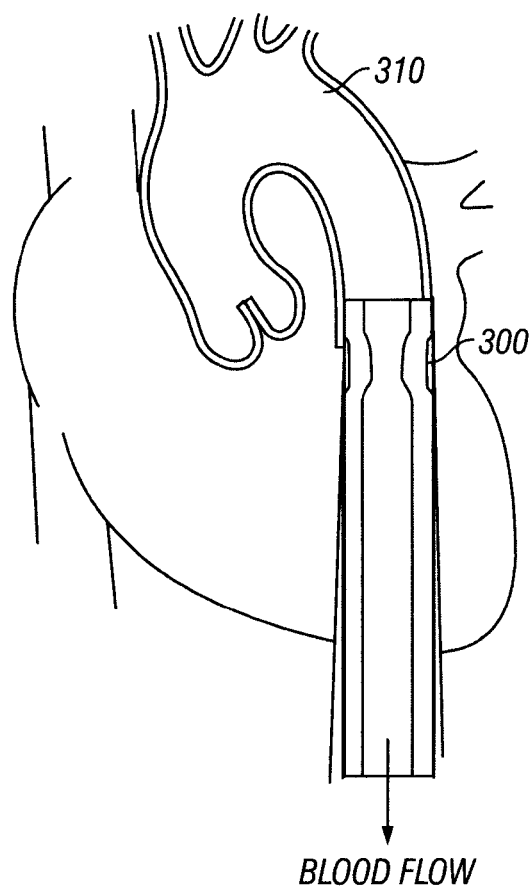
FIG. 3 shows the pump in place inside the aorta.
Figure 4:
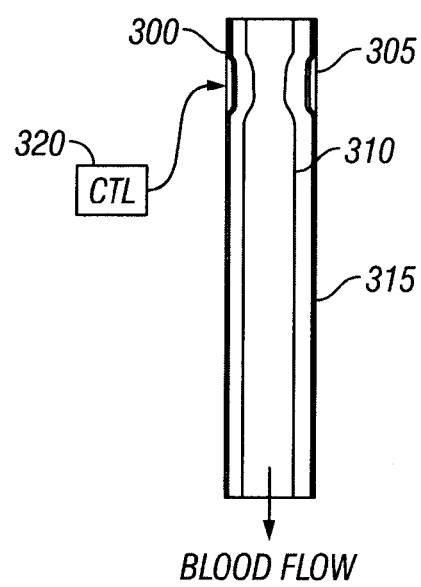
FIG. 4 illustrates a pump embodiment that is suitable for such an aorta.

FIG. 3 illustrates the pump in place inside the aorta and FIG. 4 illustrates a pump embodiment that is suitable for such an aorta. The pump 300 is shown within the aorta 310. The device can be inserted by a catheter lying against the aortic walls. The pump can be delivered through the femoral artery inserted in a collapsed state. Thereafter, a stent can be used to expand the outer lumen so that the outer rigid surface of the pump lays flush against the inner walls of the aorta. Once in position, the gelatinous material, e.g., a hydrogel, can be injected to expand the outer lumen. Since the external wall is not dynamically excited, significantly less stress is exerted on the surrounding tissue as compared with intra-aortic balloon pumps, which may exert relatively large stresses on the aorta. In this embodiment, the actuator is shown at the location 305, and the pump 300 is shown with the very elastic internal surface 310, and the compliant but not dispensable outer surface 315. The outer surface 315 is capable of inward but not outward motion. This outer surface 315 is in contact with the inside of the aortic walls.

The actuator 305 may be, for example, an electromagnetic coil. It is actuated by controller 320 to periodically restrict and relax, either locally from a source of power, or remotely via a wire to a source of power or via some wireless mechanism. It may be a piezoelectric device that causes a constriction around the inner surface 310. The actuator may alternatively be located within the gel itself.

The general structure and techniques, and more specific embodiments which can be used to effect different ways of carrying out the more general goals are described herein.

Although only a few embodiments have been disclosed in detail above, other embodiments are possible and the inventor(s) intend these to be encompassed within this specification. The specification describes specific examples to accomplish a more general goal that may be accomplished in another way. This disclosure is intended to be exemplary, and the claims are intended to cover any modification or alternative which might be predictable to a person having ordinary skill in the art. For example, the pump can be used for other applications. Different materials can be used in place of the disclosed gel. The controller can control at a periodic frequency, or can control at aperiodic pulse periods. The lumens may be cylindrical, but may also be any other shape, including elliptical in cross section, or any other shape.

Also, the inventors intend that only those claims which use the words "means for" are intended to be interpreted under 35 USC 112, sixth paragraph. Moreover, no limitations from the specification are intended to be read into any claims, unless those limitations are expressly included in the claims. The controller for the actuation that is described herein may be carried out by any kind of computer, either general purpose, or some specific purpose computer such as a workstation. The computer may be a Pentium class computer, running Windows or Linux, or may be a Macintosh computer. The computer may also be a handheld computer, such as a PDA, cellphone, or laptop.

The programs may be written in C, or Java, Brew or any other programming language. The programs may be resident on a storage medium, e.g., magnetic or optical, e.g. the computer hard drive, a removable disk or media such as a memory stick or SD media, or other removable medium. The programs may also be run over a network, for example, with a server or other machine sending signals to the local machine, which allows the local machine to carry out the operations described.

What is claimed is:

1. A pumping device, comprising:
    an outer wall formed of a substantially unbending material defining an inner surface that defines an outer boundary of a first lumen inside the outer wall and an outer surface outside the outer wall, said outer wall configured to be implanted in and reside within a body cavity;
    an inner wall, disposed entirely within said first lumen, said inner wall having an outer surface that defines an inner boundary of said first lumen and an inner surface that defines an outer boundary of a second lumen, said inner wall formed of a material that is elastically deformable;
    a fluid material, filling said first lumen between said inner wall and said outer wall, said fluid material having a mechanical property that makes said fluid material adapted to transmit applied force waves; and
    an actuator, that actuates said fluid material to create motion in the fluid material at a frequency that causes constructive wave interaction within the fluid material and adapted to drive a fluid flow through said second lumen; and
    a controller, that controls the actuator to produce a lower amplitude actuation of said fluid material at said frequency, where said actuation at said frequency produces a higher amplitude actuating of said first lumen, where said higher amplitude of the actuation of the first lumen is greater than said lower amplitude of actuation of said material, wherein said controller controls the lower amplitude actuation to said frequency that constructively interferes, to create the higher amplitude actuation, and wherein said frequency of said lower amplitude actuation is a resonant frequency that causes a resonant effect in the fluid material, to create said higher amplitude actuation.

2. A device as in claim 1, further comprising another lumen section, connected to said second lumen, where said another lumen section has a different fluidic characteristic than said second lumen.

3. A device as in claim 1, wherein said actuator creates an excitation force in the material sonically.

4. A device as in claim 3, wherein said actuator controls the lower amplitude waves to a frequency that constructively interferes, to create the higher amplitude wave.

5. A device as in claim 4, wherein said actuator forms a surface wave on said outer wall.

6. A device as in claim 3, wherein said actuator forms a surface wave on said outer wall.

7. A device as in claim 1, wherein said actuator is located between said inner wall and said outer wall.

8. A device as in claim 7, wherein said actuator is located within the fluid material.

9. A device as in claim 1, wherein at least one of said inner wall and said outer wall has a closed end.

10. A device as in claim 1, wherein at least one of said inner wall and said outer wall have open ends.

11. A device as in claim 1, wherein said fluid material is a hydrogel.

12. A device as in claim 1, wherein said fluid material has the viscosity of a gel having a viscocity higher than 1.5 centi-Poise.

13. A device as in claim 1, wherein said inner and outer walls are each substantially cylindrical.

* * * * *